United States Patent [19]

Hoffmann et al.

[11] Patent Number: 5,254,348
[45] Date of Patent: Oct. 19, 1993

[54] TRANSDERMAL THERAPEUTIC SYSTEM COMPRISING TULOBUTEROL AS ACTIVE SUBSTANCE

[75] Inventors: Hans R. Hoffmann; Michael Horstmann, both of Neuwied, Fed. Rep. of Germany

[73] Assignee: LTS Lohmann Therapie Systeme GmbH & Co. KG, Neuwied, Fed. Rep. of Germany

[21] Appl. No.: 646,560

[22] Filed: Jan. 28, 1991

[30] Foreign Application Priority Data

Jan. 26, 1990 [DE] Fed. Rep. of Germany ....... 4002481

[51] Int. Cl.$^5$ ............................................. A61F 13/02
[52] U.S. Cl. ..................... 424/449; 424/448; 424/489
[58] Field of Search .................. 424/448, 449, 489

[56] References Cited

U.S. PATENT DOCUMENTS

| | | | |
|---|---|---|---|
| 4,655,768 | 4/1987 | Marecki | 604/897 |
| 4,769,028 | 9/1988 | Hoffmann | 424/443 |
| 4,781,924 | 11/1988 | Lee | 424/449 |
| 4,842,866 | 6/1989 | Horder | 424/468 |

*Primary Examiner*—Thurman K. Page
*Assistant Examiner*—D. Gabrielle Phelan
*Attorney, Agent, or Firm*—Sprung Horn Kramer & Woods

[57] ABSTRACT

The present invention relates to a transdermal therapeutic system with tulobuterol or one of the pharmaceutically acceptable salts thereof as active substance, comprising a backing layer which is substantially impermeable to active substances and at least one matrix layer which contains the active substance, which matrix layer comprises at least one styrene-1,3-diene-styrene block copolymer. The present invention is further directed to a process for the production of said transdermal therapeutic system.

9 Claims, No Drawings

TRANSDERMAL THERAPEUTIC SYSTEM COMPRISING TULOBUTEROL AS ACTIVE SUBSTANCE

DESCRIPTION

The present invention relates to an active substance containing skin patch for the treatment of bronchial asthma with the active substance tulobuterol: it further relates to a process for the production of said cutaneous patch. The embodiments according to the present invention, which consist of a backing layer which is substantially impermeable to the active substance and a pressure-sensitive adhesive matrix layer containing the active substance, exhibit a matrix comprising at least one styrene-1,3-diene-styrene block copolymer. The manufacture of the active-substance-containing adhesive layer by means of a hotmelt coating process is described as the particularly preferred production method.

Transdermal therapeutic systems (TTS) are self-adhesive pharmaceutical preparations which are to be applied to the skin, have a fixed application area, and release a drug to the human or animal body in a controlled manner with respect to time and amount. Such systems are described, e.g., by Y. W. Chien, Drug Dev. Ind. Pharm. 13, 589 to 651 (1987) and have proved successful in therapy for years. Conventional types of transdermal systems already used in practice are:

a) a structure comprising an impermeable backing layer and a second layer simultaneously serving as drug reservoir, pressure-sensitive adhesive, and controlling unit, b) a composition of backing layer, drug reservoir, controlling unit, and adhesive layer in spatial separation, c) a structure comprising a backing layer and an active substance containing matrix arranged in a multi-layered form, whereby the active substance concentration becomes lower from layer to layer towards the skin, d) a composition of backing layer and matrix, whereby the release is controlled by microcapsules which are dispersed through the matrix and contain active substance.

Compared to traditional forms of application, the therapeutic progress of these systems lies in the fact that the active substance is not applied to the body in boli, such as is the case, for example, when tablets are taken, but in a continuous way.

By this, on the one hand, the duration of effect of the drug is prolonged, on the other hand, side effects are substantially avoided by the prevention of unnecessary blood level peaks.

Particularly if bronchial asthma is a chronic disease, achieving a permanent medicinal protection is of special advantage.

Active substances suitable in the asthma therapy are $\beta$-adrenergics (terbutaline, salbutamol), broncho-spasmolytics (theophylline, ethophylline), mast cell stabilizers (cromoglicic acid, ketotifen), parasympatholytics (ipratropium bromide) and corticosteroids (betametasone, beclometasone).

While many of these substances in the form of controlled dosage aerosols have proved successful in the therapy of an acute asthmatic attack, the maintenance therapy of this disease, for example, with orally administered $\beta$-adrenergics, still is unsatisfactory.

These substances cause raised pulse rate and increase in blood pressure, in particular if the blood levels are higher than therapeutically necessary. Exactly for said range of indications, the application of transdermal therapeutic systems would be particularly advantageous. Above all, it would comply with the want of asthmatic patients for carrying with them an efficient and perceptible medicinal long-term prophylaxis.

Unfortunately, only few drugs are suitable for the use in transdermal therapeutic systems. This is due to many reasons. Insufficient chemical and structural suitability, too high therapeutic daily doses, chemical instability are only some of these reasons. Thus, due to these and other reasons, no asthma-TTS is on the market until now.

The transdermal administration of terbutaline is known from DE-OS 37 32 642, that of salbutamol from EP-A 306 926, and that of clenbuterol from EP-A 227 836. These active substances are $\beta$-adrenergics having in common some chemical structural elements with the active substance tulobuterol. However, they are substantially different with respect to pharmacokinetics, their pharmaceutical composition, and the required therapeutic daily dose.

For example, the inherent duration of action of clenbuterol (biological half-life approximately 35 hours) is much too long. Due to this reason, the risk of cumulation is very high even if administered orally thus rendering it unsuitable for the transdermal administration.

The Japanese publication No. 63-10716 describes a topical remedy comprising as active component a $\beta$-stimulant, such as, clenbuterol, salbutamol, procaterol, and tulobuterol. In this connection, tulobuterol is dissolved, amongst others, in an acrylate/methacrylate-copolymer, the mixture applied to a cotton cloth, and dried to form a film, in order to obtain a paste pressure-sensitive-adhesive label.

A percutaneous preparation of tulobuterol is known from EP-A 0 374 980, in which the active substance is contained in a polyisobutylene matrix applied to a backing layer. The use of polyisobutylene as carrier for the active substance is said to have a favourable influence on the release rate and on the stability of tulobuterol without having to use other known additives.

In view of this state of the art, the object of the present invention is to provide a transdermal therapeutic system suitable for the asthma therapy and comprising tulobuterol as active substance, which permits a simplified production and handling thereby avoiding loss of active substance, safe dosage of the active substance with optimal release rate and tolerance.

According to the present invention this object is achieved by a transdermal therapeutic system comprising as active substance tulobuterol (2-tert butylamino)-1-(2'-chlorophenyl)-ethanol) or one of the salts thereof in a matrix containing at least one polystyrene-1,3-diene-polystyrene block copolymer.

Unexpectedly, and up to now unknown, the $\beta$-adrenergic active substance tulobuterol possesses a combination of properties which makes it almost destined for the use in a TTS. Among others, these properties are the favorable combination of being readily soluble in organic solvents with water-solubility still present, the remarkable chemical stability which—even at temperatures above 160° C.—did not lead to a calorimetrically detectable decomposition, and the high effectiveness of the substance (approximately 3 to 5 mg per day).

The transdermal therapeutic system according to the present invention preferably exhibits a backing layer which is substantially impermeable to active substances and at least one matrix layer comprising the active substance and containing at least one styrene-1,3-diene-styrene block copolymer. In addition to the active substance containing layer or layers, the system may comprise one or more layers towards the skin side which are substantially free from active substance. Furthermore, the layers of the system may be of different thicknesses, and may differ in their pharmaceutical composition, in particular with respect to the composition of the auxiliary agents. The active substance may be homogeneously distributed within the matrix layer, preferably effected by dissolution. It may also be present as solid matter within the matrix in finely dispersed suspension, whereby particle sizes of the active substance between 1 and 100 μm are preferred.

Adjuvants suitable for the use of the active substance in the TTS having a matrix containing at least one styrene-1,3-diene-styrene block copolymer are known to the skilled artisan, for example, polymers, tackifying resins, antioxidants, softeners, fillers, solubilizers, "melt-on-auxiliaries", emulsifiers, and other substances.

Important polymers contributing to the structural-mechanical stability (cohesion) are styrene-1,3-diene-styrene block copolymers, in particular styrene-butadiene-styrene-, and styrene-isoprene-styrene block copolymers.

In order to coordinate mechanical properties, adhesiveness and cohesion it may be advantageous to admix to the aforementioned block copolymers copolymers of esters and amides of the acrylic and methacrylic acid, polyvinyl esters of fatty acids, polyvinyl ethyl- or -isobutyl ethers, 1,2-propanediol-adipic-acid-esters, natural or synthetic rubbers, polyolefins, isobutylene-isoprene copolymers, polyethylene, cellulose derivatives, such as ethyl cellulose or cellulose acetate phthalate.

Suitable tackifying resins, for example, are benzoin resin, dammar resin, copal, montanic acid ester, sandarac resin, shellac, aliphatic hydrocarbon resins, esters of (hydrogenated) collophony or (hydrogenated) abietyl alcohol, respectively, derivatives of betapinene, polyolefin resins, coumarone-indene-resins.

Antioxidants in general serve as protection against the influence of atmospheric oxygen. Some examples thereof are: butylhydroxyanisole, butylated hydroxytoluene, delta-tocopherol, gamma-tocopherol (-acetate), octyl gallate, L-ascorbic acid, ascorbic palmitate.

Fillers, such as titanium dioxide, chalk, bentonite, calcium phosphate, kaolin, lactose, colloidal silica, talcum, magnesium carbonate, may be contained, as well as water-swellable substances, such as xanthene, pectin, starch and the derivatives thereof, cellulose and the derivatives thereof, carrageen, dextrin, tragacanth, polyvinylpyrrolidone, gelatin, gum arabic, carob flour, and other substances, as well as mixtures of such materials.

Examples of solubilizers and plasticizers are fatty acids, triglycerides, paraffins, ethyloleate, and other fatty acid esters of linear mono- or multivalent alcohols, octanol, and other medium-chain alcohols, phthalic acid ester, mineral oil, glycerol, propylene glycol, mono- and diglycerides of edible fatty acids, sodium lauryl sulfate, polyoxyethylene alkyl ether, polyoxyethylene, lecithin, or polyoxyethylene-sorbitan-ester.

The transdermal therapeutic system according to the present invention is manufactured according to a process which is as well covered by the present invention.

In this connection, adhesive, active substance, and other adjuvants are commonly dissolved in a suitable solvent and applied to the backing layer, for example, by means of a coating procedure. The solvent is subsequently removed from the backing layer by drying, and the backing layer is transformed to a semirigid, adhesive consistency. It is possible too, to spread said solvent-containing mass on a release liner (with dehesive finish), dry it adequately, and subsequently transfer it to the final backing layer by means of lamination coating.

In this connection, it may be advantageous to laminate several active-substance-containing layers or active-substance-free layers on top of each other, for instance, to provide extremely high area concentrations of active substance within a TTS. In general, however, a charge of 8 to 30 mg on a surface of 10 to 35 cm² is absolutely sufficient.

In addition, tulobuterol is so stable that many other special processes to imprint or spray on a foil or nonwoven, and other dosage methods are suitable for the manufacture of a TTS. However, the so-called hotmelt coating process is to be mentioned here in particular. In this process, tulobuterol and the adjuvants are melted together without the use of solvents and this homogeneous mass, which state is effected by means of kneading, if necessary, is applied to the backing layer or a dehesive foil in the heat. Heated extruders with slot-shaped discharge extruder die known from plastics processing are suitable for this purpose. This process is advantageous since solvent is saved and high energy costs, which always arise when solvent-containing films are dried, avoided. To achieve the purpose according to the present invention, there are two possible ways: to bring the completely dissolved active substance into the adhesive matrix, or to distribute part of the substance in the form of a finely divided suspension within the basic mass.

The invention will be illustrated by the following examples which, however, do not constitute a limitation of the present invention:

EXAMPLE 1

157.3 g polyisobutylene average molecular weight appr. 1,270,000 (e.g., Oppanol® B 100) solution (21.3% g/g) in benzine 33.7 g polyisobutylene average molecular weight appr. 40,000 (e.g., Oppanol® B 10)

16.5 g polyisobutylene average molecular weight appr. 800 (e.g., Oppanol® B 3)

16.5 g thermoplastic hydrocarbon resin (e.g., Escorez® 5300)

are dissolved under stirring in 110.7 g n-hexane

In a cylindrical glass vessel 0.96 g tulobuterol base are added to 60.0 g of this solution. The solution is stirred by means of a magnetic stirrer until it is completely dissolved.

The solution is spread on a siliconized polyester foil (thickness 100 μm) at a layer thickness of 300 μm. Drying was effected in five stages. The tulobuterol content of a punched piece taken from each stage was determined by High Pressure Liquid Chromatography (silica-gel, UV-detection at 210 nm):

| Conditions | Content (mg/cm²) |
| --- | --- |
| Room temperature, 10 minutes | 0.34 |

-continued

| Conditions | Content (mg/cm²) |
|---|---|
| additional 60° C., 20 minutes | 0.29 |
| additional 80° C., 10 minutes | 0.17 |
| additional 80° C., 20 minutes | 0.06 |
| additional 80° C., 30 minutes | 0.01 |

Thus the drying conditions required to almost completely remove the solvent inevitably result in considerable evaporative loss of active substance. This is highly undesirable with respect to dosage accuracy, industrial safety, and environmental control.

EXAMPLE 2

0.450 g tulobuterol base
4.47 g solid resin, copolymers of diolefins and olefins (e.g., Escorez ® 4401)
15,53 g polystyrene-polyisoprene-polystyrene block copolymer (e.g., Cariflex ® TR 1107) —19.2% solution in benzineare stirred until the active substance and the resin are completely dissolved. siliconized polyester foil (100 micrometers) at a layer thickness of 300 micrometers. Ventilation for 10 minutes at room temperature was followed by final drying at 50° C. for 20 minutes.

Gravimetric analysis resulted in an area weight of the applied dry adhesive mass of 60 g/m² corresponding to an active substance content of 0.87 mg/2.54 cm² and 5.5 mg/16 cm², respectively. The backing layer (a clear polyester foil of 15 micrometer thickness) is applied by means of a laminating apparatus.

Transdermal therapeutic systems of desired size can be punched out of this laminate, too. After removal of the siliconized polyester foil, the TTS exhibited an adhesiveness on human skin sufficient for at least 24 h.

EXAMPLE 2a 4.51 g solid resin, copolymer of diolefins and olefins (e.g., Escorez ® 4401)
2.99 g styrene-isoprene-styrene block copolymer (e.g., Cariflex ® TR 1107)

are mixed and maintained at a temperature of 140° C. within a cylindrical metal vessel (inside diameter 36 mm) for one hour. The mass is stirred at 100 revolutions per minute by means of a cylindrical screw mixer (outside diameter 33 mm), whereby the mass is cooled down to 90° C. within 30 minutes. (The mass has a viscosity of approximately 2,000 dPas, measured at 140° C.; Haake Viskotester VT-02).

After one hour of rapid stirring at 250 r.p.m.,
0.44 g tulobuterol base
is added. The mass is subsequently stirred at 250 r.p.m. at 110° C. for 20 minutes. A clear spreadable polymer mass (viscosity appr. 900 dPas at 120° C.) results. About 5 g of this mass is placed between two siliconized polyester foils and pre-heated to 110° C. (however, the mass can still be handled at 80° to 90° C.). This sandwich is formed to an even laminate by drawing it between a steel plate which is preheated to 100° C. and a steel edge with diagonal ground surface at a gap width of 400 µm. Gravimetric analysis resulted in an area weight of the pure adhesive mass of 242 g/m² corresponding to an active substance content of 3.4 mg/2.54 cm² and 21.4 mg/16 cm², respectively. One of the siliconized polyester foils is removed and the final backing layer (a clear polyester foil of 15 µm thickness) applied by lamination coating.

Evaporative losses of active substance are practically excluded from the start in the aforementioned process, since the thin layer of adhesive mass never becomes exposed. Except for that and the larger layer thickness, the properties of this formulation correspond to those of Example 2, in particular with respect to adhesiveness and cohesion.

EXAMPLE 3

Active substance release

Pieces of 16 cm² size were punched out of the transdermal therapeutic systems. The active substance release was determined according to the following method: (Example 1: prior art: Example 2, 2a according to the present invention; Example 6; active substance salbutamol prior art).

In a tightly sealed cylindrical glass vessel the TTS is placed in 100 ml physiological saline and incubated at 37° C. under slight agitation (shaking water bath). After 2, 4, and 8 hours the medium is exchanged. The aqueous solutions resulting after these periods and those obtained after 24 hours are examined with respect to their tulobuterol or salbutamol content. This is carried out by means of a spectrophotometric measurement of the sample solutions in comparison with an active substance standard solution produced in the same manner and with the same medium at a wavelength of 210 nm. Physiological saline is used for zero range balancing. After addition of the detected quantities, the following values were obtained:

| TTS according to | mg/16 cm² released | | | |
|---|---|---|---|---|
|  | after 2 h | 4 h | 8 h | 24 h |
| Example 1 | 2.08 | 2.98 | 4.01 | 4.97 |
| Example 2 | 2.12 | 3.11 | 4.17 | 4.79 |
| Example 2a | 2.19 | 3.11 | 4.51 | 8.04 |
| Example 6 (salbutamol) | 0.59 | 0.64 | 0.69 | 0.74 |

EXAMPLE 4

Active substance permeation through animal skin in vitro

Circular pieces of 2.54 cm² size were punched out of the TTS manufactured according to Example 3. The active substance permeation through isolated hairless mice skin in vitro was determined according to the following method:

The TTS is centrally placed on the outer side of a piece of mice skin and clamped into a permeation cell, the basic construction thereof is described, e.g., by Kondo et al., J. Pharmacobio.-Dyn. 10, 662 to 668 (1987). The glass apparatus in use contains as acceptor medium approximately 20 ml physiological saline; it is maintained at 37° C. by means of a temperature adjustment device. The medium is replaced after 8 hours. The resulting aqueous solutions and those obtained after 24 hours are examined with respect to their tulobuterol and salbutamol content, respectively, by means of High Pressure Liquid Chromatography. In this connection, a reverse-phase-silica-gel-column equipped with a UV-detector at a wavelength of 215 nm is used. Quantification is carried out by comparing the evaluation of the peak areas with a correspondingly produced active substance standard. The following values were obtained:

| TTS according | Permeation mg/2.54 cm² | |
| --- | --- | --- |
| to | after 8 h | after 24 h |
| Example 1 | 0.55 | 0.73 |
| Example 2 | 0.45 | 0.741 |
| Example 2a | 0.52 | 1.13 |
| Example 6 (salbutamol) | 0.04 | 0.11 |

EXAMPLE 5

3.98 g solid resin, copolymer of diolefins and olefins (e.g., Escorez ® 4401)

3.25 g styrene-isoprene-styrene block copolymer (e.g., Cariflex ® TR 1107)

0.83 g polyisobutylene average molecular weight appr. 800 (e.g., Oppanol ® B 3)

are stirred in an apparatus corresponding to that of Example 2a at a temperature of 160° C. at 100 r.p.m. for one hour and subsequently cooled down to approximately 90° C.

0.21 g tulobuterol base is added. The mass is further stirred at 250 r.p.m. at 120° C. for 20 minutes. A clear spreadable polymer mass results.

In accordance with Example 2, the material is manufactured into adhesive plasters with a clear polyester foil of 15 μm thickness as backing layer. The patches have an optically perfect, clear transparent appearance and exhibit good adhesive properties on the skin.

EXAMPLE 6

4.50 g solid resin, copolymer of diolefins and olefins (e.g., Escorez ® 4401)

15.50 g styrene-isoprene-styrene block copolymer (e.g., Cariflex ® TR 1107) solution 19.2% (g/g) in benzine are stirred in a cylindrical glass vessel (inside diameter 4 cm) until the resin is completely dissolved.

0.45 salbutamol base is added and stirring continued with a magnetic stirrer.

(The mixture did not lead to a satisfying result, since—as was to be expected—the active substance was nearly insoluble).

The active substance particles which were obviously still agglomerated were dispersed in a vibrating mill—subsequently the dispersion was spread out, dried and laminated under the same conditions as described in Example 2. The result was an area weight of the dry adhesive mass of 62 g/m² and thus an active substance content of 0.89 mg/2.54 cm² and 5.63 mg/16 cm², respectively.

The adhesive mass of the patches remains cloudy even after drying due to dispersed active substance particles. In comparison with the masses according to Examples 2 and 2a this mass is poorly adhesive.

EVALUATION OF THE EXAMPLES

To form clear patches with good self-adhesive properties on the skin, the system according to the present invention (Examples 2, 2a, and 5) can be manufactured by both using styrene-1,3-diene-styrene block copolymers as sole polymer component (Examples 2 and 2a) and under the addition of further polymers, such as polyisobutylene (Example 5).

As is proved by Examples 3 (in-vitro-release) and 4 (permeation through isolated animal skin), Example 2 according to the present invention has an equivalent active substance release compared to the prior art (Example 1), Example 2a according to the present invention exhibits an increase of the release rate by approximately 60%. If, however, instead of using tulobuterol, the formulation (which for the rest corresponds to that of Example 2) is manufactured with salbutamol (Example 6), the active substance being less effective than tulobuterol, the active substance release remains on a low, therapeutically worthless level.

The particular technical advantages of the present invention become obvious in its suitability for solvent-free production processes which are demonstrated in Examples 2a and 5. Thus the active substance tulobuterol may be used in TTS in a particularly efficient way, thereby substantially avoiding pollution of the surrounding and the environment with active substance and solvents. It is understood that the specification and examples are illustrative but not limitative of the present invention and that other embodiments within the spirit and scope of the invention will suggest themselves to those skilled in the art.

We claim:

1. Transdermal therapeutic system with tulobuterol or one of the pharmaceutically acceptable salts thereof as active substance, comprising a backing layer which is substantially impermeable to active substances and at least one matrix layer which contains the active substance, in which transdermal therapeutic system the matrix layer a styrene-butadiene-styrene- or styrene-isoprene-styrene block copolymer.

2. The transdermal therapeutic system according to claim 1 wherein the matrix layer is self-adhesive.

3. The transdermal therapeutic system according to claim 1 wherein the active substance containing matrix layer is not self-adhesive and a separate adhesive layer being free from active substances is present.

4. The transdermal therapeutic system according to claim 1 wherein several active substance containing matrix layers are present.

5. The transdermal therapeutic system according to claim 4 wherein in case of several active substance containing matrix layers, the active substance concentration becomes lower from layer to layer towards the skin.

6. The transdermal therapeutic system according to claim 1 wherein at least one matrix layer which is free from active substance is present in addition to at least one active substance containing matrix layer comprises.

7. The transdermal therapeutic system according to claim 1 wherein the active substance is homogeneously dispersed within the matrix by complete dissolution.

8. The transdermal therapeutic system according to claim 1 wherein the active substance is present within the matrix in finely divided suspension or in microcapsules.

9. The transdermal therapeutic system according to claim 1 wherein the matrix layer comprises polymers, resins, and optionally softeners.

* * * * *

UNITED STATES PATENT AND TRADEMARK OFFICE
CERTIFICATE OF CORRECTION

PATENT NO. : 5,254,348
DATED      : October 19, 1993
INVENTOR(S): Hoffmann, et al.

It is certified that error appears in the above-indentified patent and that said Letters Patent is hereby corrected as shown below:

Title Page        [30] Foreign Application Priority Data:
                  Delete " 4002481 " and substitute
                  -- 4002281 --

Col. 8, line 34   After " layer " insert -- comprises --

Col. 8, line 53   Delete " comprises "

Signed and Sealed this

Eleventh Day of April, 1995

Attest:

BRUCE LEHMAN

Attesting Officer    Commissioner of Patents and Trademarks